United States Patent [19]

Cecchi et al.

[11] Patent Number: 5,096,293
[45] Date of Patent: Mar. 17, 1992

[54] DIFFERENTIAL FLUORESCENCE LIDAR AND ASSOCIATED DETECTION METHOD

[75] Inventors: Giovanna Cecchi, Vaglia; Luca Pantani, Florence, both of Italy

[73] Assignee: Consiglio Nazionale delle Ricerche, State Body, Rome, Italy

[21] Appl. No.: 583,834

[22] Filed: Sep. 17, 1990

[30] Foreign Application Priority Data

Sep. 20, 1989 [IT] Italy .................. 9528 A/89

[51] Int. Cl.$^5$ .................. G01N 21/64; G01J 3/443
[52] U.S. Cl. .................. 356/318; 250/458.1
[58] Field of Search .................. 356/317, 318, 417; 250/458.1, 459.1, 461.1, 461.2

[56] References Cited

U.S. PATENT DOCUMENTS 4,959,549  9/1990  Haub et al. .................. 356/461.1

Primary Examiner—F. L. Evans
Attorney, Agent, or Firm—McGlew & Tuttle

[57] ABSTRACT

The multichannel fluorescence lidar comprises a source for the emission of a laser beam, an optical receiving system to focus the backscattered radiation, an optical channels separator and means for processing the detected signals. The device comprises means (15) for forming the ratio, two by two, of the signals originating from the optical channels separator (11), and means (17, 19) for making the comparison between the values of the ratios and a series of values stored in an archive or a data base (21).

8 Claims, 1 Drawing Sheet

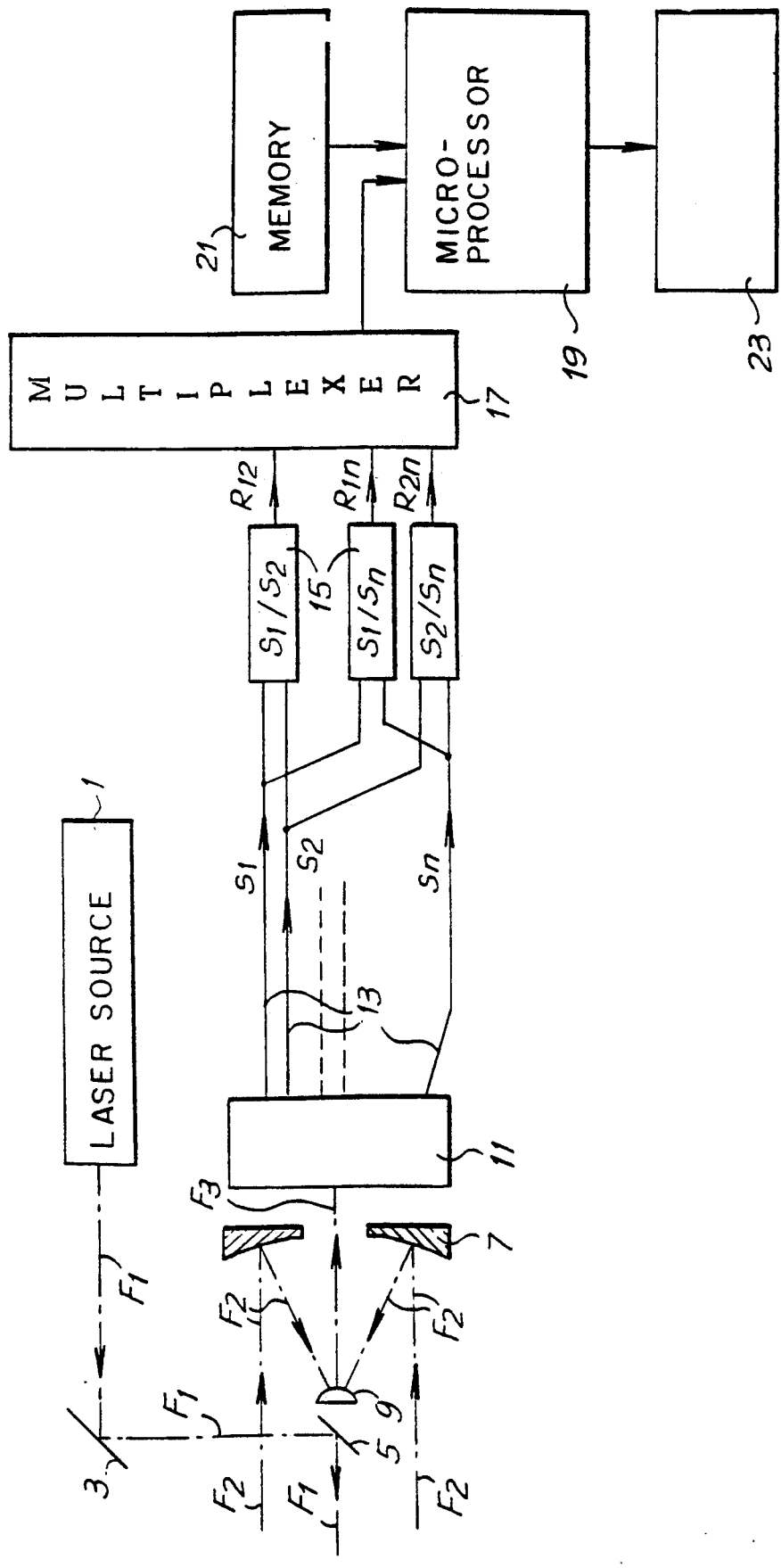

DIFFERENTIAL FLUORESCENCE LIDAR AND ASSOCIATED DETECTION METHOD

The invention relates to a multichannel fluorescence lidar device comprising a source for the emission of a laser beam, an optical receiving system to focus the backscattered radiation, an optical channels separator and means for processing the detected signals.

The invention further relates to a method of remote sensing using a multichannel fluorescence lidar, comprising the steps of: stimulating the emission of fluorescence radiation from the target; collecting the fluorescence radiation emitted by the target; separating the backscattered fluorescence radiation into a plurality of channels corresponding to predetermined emission bands; and processing the signals obtained in order to extract information concerning the target.

FIELD OF THE INVENTION

The lidar, or laser radar, is a remote sensing system composed of a laser which illuminates a target, an optical system which collects the radiation backscattered from the target and a system for analyzing the backscattered radiation. In the case of a fluorescence lidar, the individual identification of the target and/or of some of its characteristic features is undertaken by the analysis of the fluorescence radiation emitted by said target when it is stimulated by the laser radiation. The fluorescence lidar is used, in particular, in the remote sensing of water and of vegetation.

BACKGROUND OF THE INVENTION

The fluorescence lidars which are in existence at the present time detect the fluorescence radiation in certain spectral bands, which are selected by means of interference filters or of a grating spectrometer, and subsequently analyze the data extracted for the purpose of undertaking the individual identification of the target and/or of its characteristic features. The lidars of known type exhibit certain disadvantages, which are due, in particular, to the fact that the detected signals are proportional to the intensity of the radiation reflected back in correspondence with certain specific wavelengths. The signals are always influenced by spurious factors such as absorption by the atmosphere, the surface roughness of the target, the losses due to the detection system, which modify the intensity thereof and which thus make a direct detection impossible. In the systems which are in current use, it is therefore necessary to make use of a reference signal, for example an emission line of known intensity, to correct the detected signals and to permit the subsequent processing.

SUMMARY AND OBJECTS OF THE INVENTION

The subject of the invention is a lidar system which does not exhibit these disadvantages and which, in particular, permits a rapid detection and a real-time or quasi-real-time processing of the detected data without the need to correct the detected signals in order to take account of any possible spurious factors.

These and other advantages, which will become clear to persons skilled in the art on reading the text which follows, are obtained substantially with a lidar of the abovementioned type, which further comprises means for forming the ratio, two by two, of the signals originating from the optical channels separator, and means for making the comparison between the values of said ratios and a series of values stored in an archive or data base. The device according to the invention undertakes a detection, a separation of the signal into a plurality of channels and then forms a ratio between the signals available on each channel. The values of the ratios which are obtained are directly compared with a series of values which are predetermined and contained in an appropriate archive or data base. Thus, the signals do not need to be subjected to any defferred processing, but can have their ratio formed and can be directly compared in order to permit, if required, a real-time identification of the target. The ratios between the signals are virtually immune from spurious factors such as, for example, the greater or lesser absorption by the atmosphere, the roughness of the target, the losses due to the system and the like. In this way, the detection may be undertaken without the use of a reference signal.

Particularly advantageous embodiments are indicated in the attached subclaims. In particular, the determination of the ratios between the signals obtained from the optical channels separator may be undertaken by means of hardware or of software, in dependence, inter alia, upon the type of separator which is employed. The latter may make use of a series of separated photodetectors, or alternatively an array or matrix of photodetectors which is constructed using CCD technology and controlled by a central unit, in which case it is possible to obtain a number of channels which is very large and may even exceed one thousand. This is particularly advantageous in the case where it is desired to make not only measurements on fluoresce radiation signals but also measurements on the passive signal, that is to say on the radiation reflected by the target. In fact, the wavelengths of the reflected radiation and the wavelengths of the fluorescence radiations fall within a rather wide range and the normal channel separators provide a number of channels which is limited and not sufficient to detect the signal corresponding to a sufficiently large number of wavelengths, so as to provide significant data both concerning the fluorescence emission and concerning the reflection emission. The separator incorporating an array of photodetectors may, on the other hand, provide a large number of channels and thus permit the analysis both of the fluorescence signal and of the reflection signal (passive signal).

The invention further provides a method of the abovementioned type which permits a real-time or quasireal-time processing of the detected data without being influenced by spurious factors.

The method according to the invention is essentially defined in that the signals obtained from the separation of the backscattered radiation have their ratio formed, two by two, in order to obtain one or more values of ratios of signals, which are compared with values of ratios which are predetermined and stored, corresponding to defined targets or categories of targets. The processing may take place in real time or quasi-real time, but may also be undertaken on a deferred basis.

BRIEF DESCRIPTION OF THE DRAWINGS

The invention will be better understood with reference to the description and the accompanying drawing, which shows a practical non-limiting illustrative embodiment of said invention. The single FIGURE of the drawing shows a diagram of the operation of the device according to the invention.

DETAILED DESCRIPTION OF THE PREFERRED EMBODIMENT

In the drawing, the reference numeral 1 diagrammatically indicates a laser source which emits a beam of radiations F1, which is reflected by a system of mirrors 3, 5 towards the target (not shown). The target, excited by the laser radiation, emits by fluorescence a backscattered radiation F2, which is collected by an optical system 7, 9 of known type. The focused beam F3 is passed to an optical channels separator 11 which may be constructed in accordance with any of the techniques which are conventional for this type of devices. In particular, the separator 11 may be constructed by means of separate photodetectors associated with a dispersion system or alternatively by means of an array of photodetectors in accordance with CCD engineering.

The separator 11 separates the signal into n electrical signals S1, S2, ... Sn which are proportional to the intensity of the fluorescence radiation detected in each predetermined specific band. The number of channels of the separator, and thus the number of signals S1, ... Sn which are obtained at the output of the separator 11, may vary from a few tens to some hundreds, depending upon the technology employed to construct said separator. The signals S1, ... Sn have their ratio formed in order to obtain a series of signals R12, ... R1n, R21, ... Rnn, where $$Rij = Si/Sj$$

The ratios Rij may be obtained by means of hardware, for example by means of operational amplifiers or other circuit components, and then converted into digital signals, or alternatively by means of software, with analog/digital conversion of the signals S1, ... Sn. In the drawing, the reference numeral 15 generally indicates functional units which form (by means of software or by means of hardware) the ratios between the signals S1, ... Sj and execute the anologic/digital conversion. The signals Rij obtained in this manner are passed to a multiplexer 17 and from the latter to a microprocessor 19, to which data stored in a memory 21 are also supplied, in order to undertake the analysis of the detected signals. In particular, the memory 21 contains an archive of data comprising a series of values of ratios Rij' at various wavelengths of the stimulating laser emission. Each value of the ratio Rij' corresponds to a specified target or to a category of targets which it is desired to identify individually. The comparison between the ratios Rij obtained on the basis of the signals S1, ... Sn separated by the separator 11 and the stored ratios Rij' permits the individual identification of the type or the category of target with respect to which the detection is undertaken. The comparison may be undertaken directly and without further processing of the signals S1, ... Sn which are detected, since the effects of any possible spurious factors are eliminated when the ratio between two signals Si, Sj is formed.

In order to determine and to optimize the number and the spectral position of the bands corresponding to the various channels 1, ... n of the separator 11, it is possible to proceed in the following manner:

for each type or category of targets an archive is constructed, containing fluorescence emission spectra corresponding to the wavelength selected for the excitation, i.e. corresponding to the wavelength of the stimulating radiation from the laser;

given Sk' and Sl' two intensities of the florescence signal which correspond to two specific emission wavelengths, and given "a" and "b" two targets, or categories of targets, which it is desired to distinguish, then it is desired to obtain the two wavelengths which maximize the function.

$$d(a,b) = \frac{(Rkla' - Rklb')}{(Rkla' + Rklb')}$$

summed over all the elements "a" and "b" of the set of targets which it is desired to distinguish in the detection and wear $$Rkl' = Sk'/Sl'$$

and the indices "a" and "b" indicate that the ratio relates to the target of type or category "a" and "b" respectively;

applying statistical decision criteria, a determination is made of the values of Rkl' which separate the various targets or various categories of targets. These values constitute the data of the archive contained in the memory 21 and are compared with values Rij obtained from the ratio of the signals S1, ... Sn which are detected.

If a single pair of wavelengths are not sufficient to identify reliably all the targets or categories of targets which it is desired to distinguish and which may be simultaneously present, it is necessary to group together the targets in respect of which there is ambiguity and to determine, using the criteria set forth hereinabove, another pair of wavelengths and the associated values of Rkl' for each such group.

We claim:

1. A multi-channel fluorescence lidar device comprising:

laser beam source means for emission of a laser beam pulse; optical receiving means for focussing back scattered radiation; optical channel separator means for separating a backscattered fluorescence signal corresponding to each single laser pulse into a predetermined number of channels, to form intensity signals each of said predetermined number of channels corresponding to predetermined wavelength band values, said intensity signals being proportional to the intensity of said backscattered fluorescence signal, corresponding to each single laser pulse, in each of said predetermined wavelength band values; signal processing means for receiving said intensity signals and for forming a plurality of ratio signals, said plurality of ratio signals comprising a signal based on the ratio of each intensity signal to each other intensity signal for each single laser pulse; and comparison means for comparing the value of each ratio signal to values stored in a memory.

2. A device according to claim 1, wherein said signal processing means comprises an electronic processor programmed to form said ratios by means of software.

3. A device according to claim 1, wherein said signal processing means includes a hardware circuit arrangement for forming said ratio.

4. A device according to claim 1, wherein said comparison means comprises a programmed electronic processor and a multiplexer for passing data obtained from said signal processing means.

5. A device according to claim 1, wherein said optical channel separator means comprises a matrix of CCD (charged coupled device) photo detectors controlled by a central unit.

6. A method of remote sensing using a multi-channel fluorescence lidar arrangement comprising the steps of:
stimulating the emission of fluorescence radiation from a target located at a remote location;
collecting the fluorescence radiation emitted by said target corresponding to a single stimulated emission;
separating said fluorescence radiation into a plurality of channels, to form a plurality of intensity signals each channel corresponding to a predetermined emission wavelength band;
processing each of said intensity signals obtained to form a ration of each intensity signal to each other intensity signal to form a plurality of ratio signals for each single stimulated emission; and
comparing each of said ratio signals to predetermined stored signals corresponding to defined targets or categories of targets.

7. A method according to claim 6 wherein said comparison between values of said ratios obtained from the detected signals and said stored signals is made in real time.

8. A multi-channel fluorescence lidar device comprising:
laser beam source means for emission of a laser beam pulse directed at a remote object; optical receiving means for focussing backscattered radiation from said remote object; optical channel separator for separating backscattered fluorescence radiation corresponding to each signal laser pulse into a predetermined number of channels to form a plurality of intensity signal, each of said predetermined number of channels corresponding to predetermined wavelength values, said intensity signals being proportional to the intensity of said backscattered fluorescence signal in each of said predetermined specific wavelength bands for each signal laser pulse; signal processing means for receiving said intensity signals and for forming a plurality of ratio signals, said plurality of ratio signals comprising a signal based on the ratio of each intensity signal to each other intensity signal for each single laser pulse; and comparison means for comparing the value of each ratio signal to values stored in a memory.

* * * * *